United States Patent [19]

Lagarde et al.

[11] 4,134,538
[45] Jan. 16, 1979

[54] PROCESS AND APPARATUS FOR IDENTIFICATION OF OBJECTS

[75] Inventors: Pierre Lagarde, Versailles; André Elie, Paris, both of France

[73] Assignee: La Societe Metalimphy, Paris, France

[21] Appl. No.: 778,238

[22] Filed: Mar. 16, 1977

[30] Foreign Application Priority Data

| | | |
|---|---|---|
| Mar. 18, 1976 [FR] | France | 76 07899 |
| Aug. 19, 1976 [FR] | France | 76 25182 |
| Aug. 20, 1976 [FR] | France | 76 25313 |
| Oct. 11, 1976 [FR] | France | 76 30519 |
| Oct. 11, 1976 [FR] | France | 76 30520 |

[51] Int. Cl.² ......................... G06K 7/08; G01S 9/56; G08B 21/00; G11B 25/04
[52] U.S. Cl. ..................... 235/449; 235/493; 360/2; 340/572; 343/6.5 LC
[58] Field of Search ............... 235/61.11 H, 61.12 M, 235/61.12 N, 61.12 C, 61.11 R, 61.11 D, 61.11 E; 209/DIG. 1; 340/280, 149 A, 152; 343/6.5 LC; 340/224; 360/2

[56] References Cited

U.S. PATENT DOCUMENTS

| | | | |
|---|---|---|---|
| 3,325,632 | 6/1967 | Lilly | 235/61.12 M |
| 3,699,311 | 10/1972 | Dunbar | 235/61.11 H |
| 3,755,803 | 8/1973 | Cole | 340/280 |
| 3,832,530 | 8/1974 | Reitboeck | 343/6.5 LC |
| 3,958,105 | 5/1976 | Sidlauskas | 235/61.11 H |
| 3,970,824 | 7/1976 | Walton | 235/61.11 H |
| 4,029,945 | 6/1977 | Yamada | 235/61.12 N |

*Primary Examiner*—Robert M. Kilgore
*Attorney, Agent, or Firm*—Haseltine, Lake & Waters

[57] ABSTRACT

An apparatus and process for identifying objects marked by a magnetic band or thin filament comprising detecting the passage of the magnetic band in a detection zone comprising a framework having an excitation coil fed with alternating current to produce an alternating magnetic field and a detecting coil balanced with the excitation coil such that no signal normally will appear in the absence of a magnetic body in proximity to the framework. The passage of an object carrying a magnetic band in proximity to the framework producing for each alternation of the excitation field an unbalance in a detecting circuit and the appearance of a signal which is fed to apparatus for the detection and measurement of the phase of the signal with respect to the excitation field. The magnetic band is selectively divided at variable predetermined locations by cuts of variable predetermined extent such that at the time of passage of the bands proximate the detection zone, signals of variable amplitudes are also produced, the decoding of the signals being effected in the detection apparatus by measurement of their amplitude.

11 Claims, 8 Drawing Figures

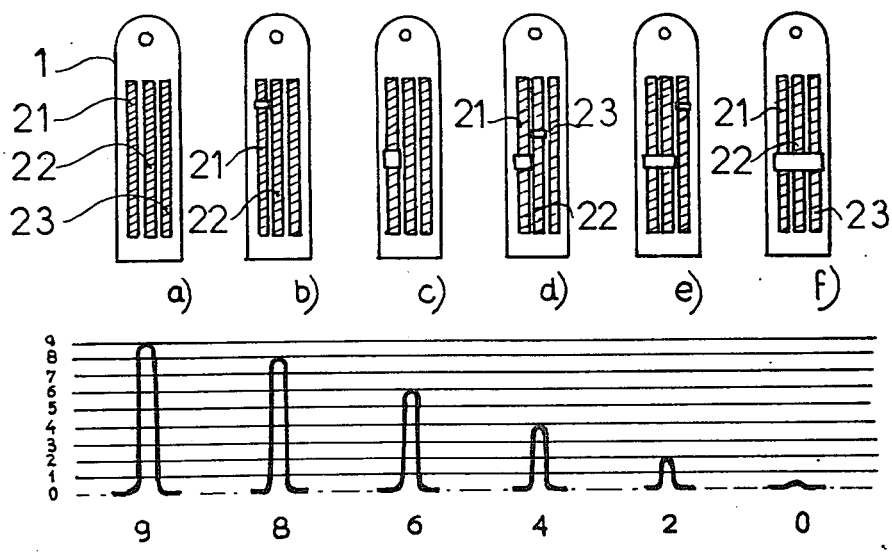
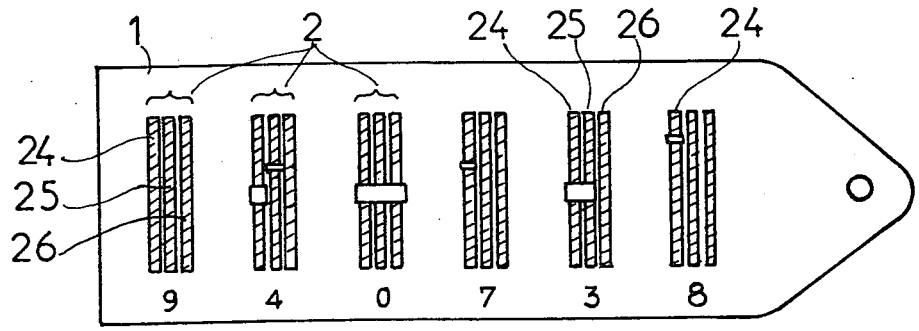

PROCESS AND APPARATUS FOR IDENTIFICATION OF OBJECTS

FIELD OF THE INVENTION

The present invention relates to a process and an apparatus for the detection and the identification of coded labels carried by objects in order to initiate an operation in accordance with the detected code or in order to effect a selective ultimate treatment of these objects.

The invention finds effective application for the automatic sorting of packages or mailbags.

BACKGROUND

Processes exist for automatic location or addressing by reading conventional magnetic bands or tapes of the type used in tape recorders or by counting electroluminescent marks as for the sorting of letters. Such apparatus requires a precise position of the support with respect to the marking apparatus and generally a constant speed of displacement. They are, therefore, poorly adapted to the reading of labels carried by articles of very varied shape and orientation, such as packages or sacks.

Also known is the capability of detecting on an object the presence of a sample, even of very small size, of a metal having particular magnetic properties and without direct contact of the object with the detection apparatus.

Thus, French Pat. Nos. 763,681 and 2,055,019 disclose processes and means especially adapted to detect the theft of books from public libraries. According to these patents, there is concealed in the object to be protected a magnetic metallic band of an alloy of "permalloy" type and the users of the library must, in order to leave, pass through the interior or in the vicinity of a framework forming a detector of the presence of the concealed magnetic band. For this purpose, the framework carries an excitation coil producing an alternating magnetic field and a balancing detecting coil such that normally no signal appears. The presence in the framework of a book carrying the magnetic band causes the appearance of an unbalancing magnetic induction which unbalances the detecting coil and produces a signal that can be detected by conventional means.

Unfortunately, such apparatus, conceived primarily for anti-theft, only permits the detection in the control zone of the simple presence of a marked object. The problem posed by the automatic sorting of mail sacks or parcels is primarily to be able to identify each of the objects for subsequent distribution to different zones corresponding, for example, to the usual routing directions. Currently, the different parcels or sacks are provided with a label with an identification of the destination and the sorting is effected, most often, by an agent in front of whom the different sacks are passed and who by visual reading of the labels manipulates different levers for distributing the objects in the desired directions.

SUMMARY OF THE INVENTION

An object of the present invention is to detect the passage of a label in an alternating field not only for control of the presence of previously marked articles but also for the identification of the articles by reading the label which is previously coded and fixed to the objects.

The invention is applicable to a process for identifying objects marked by a magnetic band or tape or thin magnetic filament by detecting the passage of the magnetic band in a detection zone comprising at least one framework having an excitation coil fed with alternating current to create an alternating magnetic field and a detecting coil balanced such that no signal will appear in the absence of a magnetic body in proximity to the framework, the passage through or in proximity to the framework of an object carrying a magnetic band producing for each alternation of the excitation field, an unbalance in the detecting coil and the appearance of a signal which is applied to an apparatus for the detection and for the measurement of the phase with respect to the excitation field.

According to the invention, a reference code is assigned to an object by leaving the magnetic tape intact or by selectively dividing the tape at variable predetermined locations by cuts of predetermined variable extent, thus leading at the time of passage of the tape near the detection circuit of variable amplitudes also predetermined for the resulting signal, the decoding of the signal being effected in the detection apparatus by measuring its amplitude.

According to a particular embodiment of the invention, the object is marked with a plurality of bands or thin magnetic filaments, each having different hysteresis loops characterized by different coercive fields thereby permiting the assignment to each object of a reference code with as many characters as bands or filaments utilized; one thus assigns, respectively, each character of the reference code to a band or filament in the order of the values of their respective coercive fields, the signals corresponding to each band then appearing in the detection apparatus in the same order of dephasing as the order of the coercive fields and each with amplitudes corresponding to the values assigned at the time of coding, thus reproducing the complete code in arrangement and in amplitude.

According to another particular embodiment of the invention, composite magnetic bands are utilized each constituted by the juxtaposition of a plurality of elementary bands of identical or sufficiently close magnetic characteristics such that the pertubation or unbalancing signals will be substantially in phase and each one of the elementary bands is selectively divided in independent fashion.

The invention also contemplates apparatus which comprises means for selectively dividing each magnetic band at variable predetermined places and by cuts of varying predetermined extent and detection apparatus which comprises means for measuring the amplitude of each of the signals corresponding to each one of the bands.

According to a particular embodiment of the invention, the detection apparatus comprises three successive frameworks in the path of the objects in three perpendicular planes such that the three fields produced in the respective frameworks by the excitation coils extend in three perpendicular directions.

According to a preferred embodiment of the invention, each framework is constituted by two elementary frames disposed as Helmholtz coils thus producing a constant field between the two elementary frames.

Additionally, according to a preferred embodiment of the invention, for each elementary frame the excitation circuit comprises a main coil in the frame and an auxiliary balancing coil in series while the detection circuit comprises, in series, a main coil in the frame, an auxiliary balancing coil and a coil for output of the signal, the two auxiliary coils for balancing of a group of two elementary frames being inductively coupled by a non-iron coupling; while on the other hand, for each group of two elementary frames, the two excitation circuits are fed in parallel, whereas the two output coils constitute the primary winding of a transformer with a simple secondary at the terminals of which the signal is received.

BRIEF DESCRIPTION OF THE DRAWING

The invention will become better understood with reference to the attached drawings which illustrate various embodiments of the invention for the sorting of sacks or parcels of mail.

FIGS. 5 and 6 correspond respectively to FIGS. 2 and 3 for labels having composite bands permitting an increase in the level of detectable amplitude.

DETAILED DESCRIPTION

Figure 1:
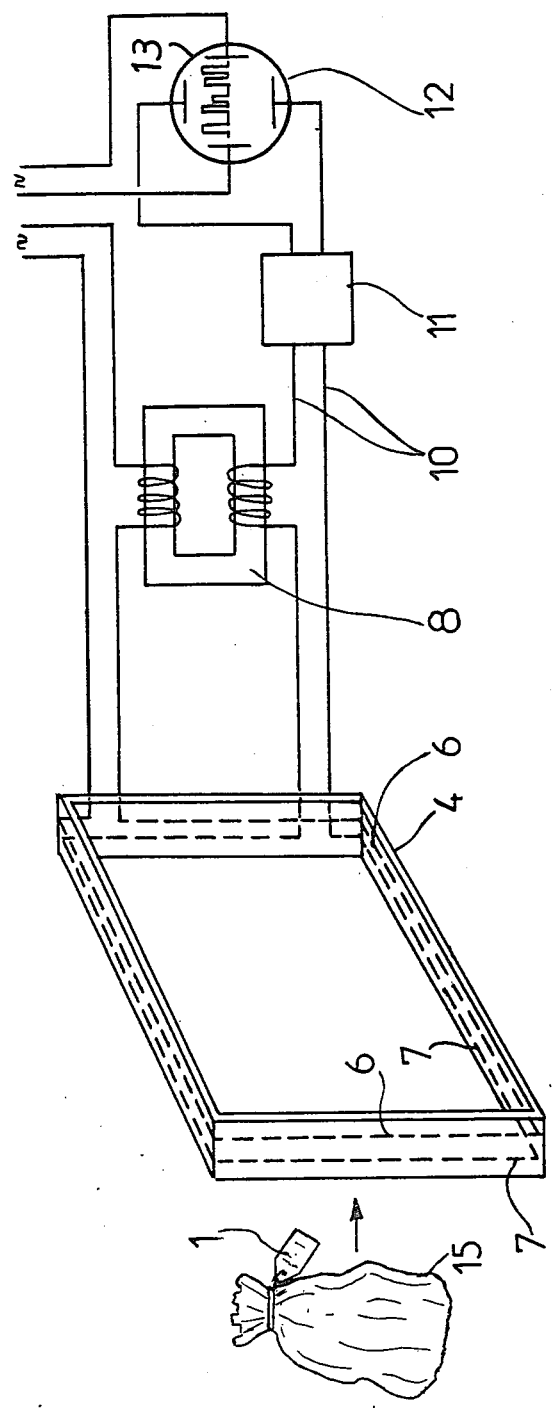
FIG. 1 is a schematic and symbolic representation of apparatus for detection and identification of coded marks on labels fixed to the parcels.

There is seen schematically in FIG. 1 the known elements of an apparatus for detection of the presence in an object of a metallic magnetic band. The objects to be detected pass through the framework which supports an excitation coil diagrammatically shown as a single winding 6 fed with alternating current. The framework 4 also carries a detecting coil shown in the same diagrammatic fashion by a winding 7. The coils 6 and 7 are connected in oppostion in a balancing circuit 8 so that no signal will appear at the output 10 in the absence of a metallic body in proximity with the framework. The output 10 is connected through the intermediary of filtering and equilibrating circuits 11 to the plates of an oscilloscope 12 which shows the detected signals.

The passage through the framework 4 of a parcel 15 carrying a coded magnetic label 1 unbalances the detector and signals 13 corresponding to the code of the label appear on the oscilloscope 12.

Of course, the representation of the apparatus for reading given here symbollically by the oscilloscope is only by way of example. It can be replaced or completed by any conventional logical decoding apparatus. The signal, thus decoded, can be utilized in conventional fashion in equipment for control of various processes and, for example, in the automatic manipulation of levers for distributing postal sacks to grouping areas corresponding to the destinations defined by the code of the label.

Figure 2:
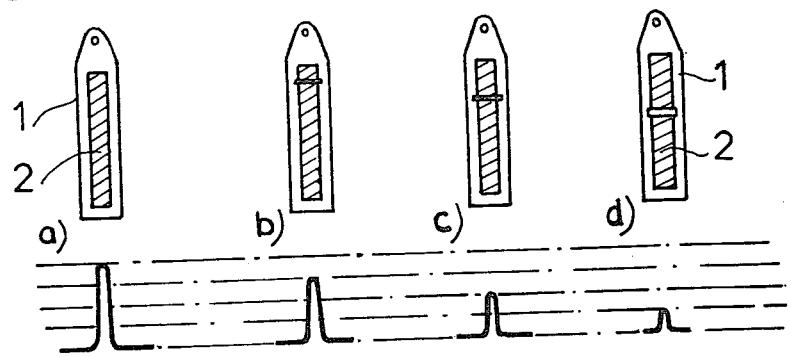
FIG. 2 shows a plurality of labels having different codings for a single magnetic band, the relative amplitudes of the signals received by the detection apparatus being illustrated for each band.

The label 1 shown in FIG. 2 is constituted by a support of paper or cardboard which can be written on in conventional fashion and it carries at the back a thin metallic band 2 of ferro-magnetic alloy having a substantially rectangular hysteresis loop, such as a piece of conventional recording tape.

The label can be introduced into a coding printer permitting local division of the metallic band by a cut of variable extent and location. Thus, at (a) the band is intact which could, for example, correspond to a value of 4, that is to say, indicate that the object carrying this label carries the sorting code 4. At (b) in FIG. 2 the band has been slightly divided near one extremity to indicate, for example, that the object carries the code 3. At (c) the cut is made further from the extremity and at (d) the cut is wide and situated towards the middle of the band; these two other forms of coding correspond, for example, to the codes 2 and 1.

The cuts of variable position and extent lead to the formation of demagnetizing fields which modify the unbalancing effect of the band in the excitation field. Therefore, they reduce the amplitude of the signal received in the detection circuit in proportion to the extent of the cut and of its position on the band. The amplitude of the signal 13 depends on the state of coding of the label, and therefore, translates the code 1, 2, 3 or 4 which carries the label.

The amplitude of the signal refers not only to the height of the signal, such as would appear on the oscilloscope but also the region which it occupies. As desired, the electronic circuits for detection could be more specifically sensitive to one or the other of these characteristics of the signals.

Figure 3:
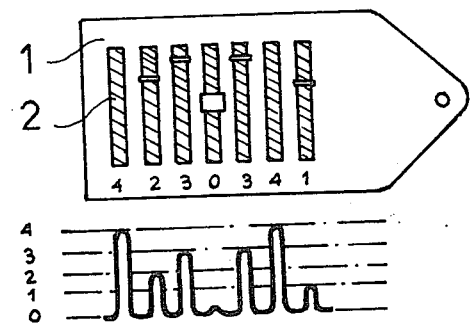
FIG. 3 shows a label having a plurality of simple magnetic hands permitting a coding with a plurality of characters and with a plurality of amplitude levels for each character.

With reference to FIG. 3, therein is seen the possibility of increasing the coding capacity by utilizing a plurality of magnetic bands on the same label. Thus, the label 1 of FIG. 3 carries seven thin metallic bands on the back.

Each band is of different ferro-magnetic alloy and has a substantially rectangular hysteresis loop. The bands 2 are arranged parallel to one another on the label in the same order as the coercive fields proper of each alloy utilized. For example, the band at the left could be of mumetal having a substantially zero coercive field, the bands to the right being of alloys whose coercive fields progressively increase, for example, to 200 oersteds. The label has been introduced in a coding printer permitting the local division of each magnetic band by a cut of variable placement and extent or leaving the band intact.

Here we have shown four types of cuts with which the absence of a cut define five levels of amplitude of the signal; one can, therefore, give to each band, for example, the values 4, 3, 2, 1 or 0. If as in FIG. 3, one assigns to the first band which is intact the signification of the number 4, one sees that the second band has a thin cut towards the extremity leading to a reduction of the amplitude of the signal by about 75% of the initial value; the second hand, thus has the signification of numeral 3.

A thin cut closer to the middle could reduce the signal to 50% and give to the band the signification of number 2; by making the thin cut closer to the middle, the amplitude of the signal could be reduced further to correspond to number 1. Finally, a large cut at the middle of the band will practically cancel the signal received and will correspond to a zero signification for the band.

Thus, it is seen that by giving five values to each band, one can with N number of bands of different magnetic properties, provide the object with N figures in base 5.

The passage through the frame work 4 of a parcel 15 carrying a magnetic label 1 with seven bands unbalances the detector and corresponding signals appear in the form of as many pulses as there are active metallic bands on the label 1. These pulses are spaced with respect to the excitation field, in accordance with the values of the coercive fields of the metal utilized. The oscilloscope shows a series of signals whose relative position reproduces the relative position of the bands 2 on the label 1. One can therefore read the transposition on the oscilloscope of the coded number on the label.

It can be noted that the altered appearance of the response signals of each band in the course of an alternation of the alternating magnetic excitation field is independent of the position of the band and, therefore, of the orientation of the label with respect to the frame; it depends only on the relative values of the respective coercive fields of each band. The appearance of the signals, or the absence of a signal, will, therefore, be made in the order of the values of the coercive fields, that is to say in the order of reading of the numerals of the number code.

Figure 4:
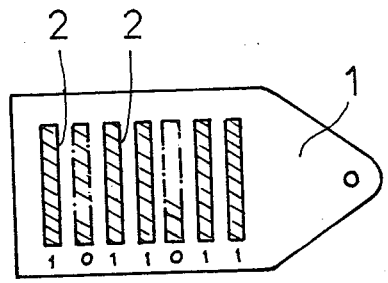
FIG. 4 is a similar label limited to a binary coding.

The label shown in FIG. 4 is a particular case of that of FIG. 3. Here each band 2 is simply maintained intact or cleanly cut at a plurality of places or cleanly removed. The signals obtained from each band are then either a full signal or a substantially zero signal. One thus realizes a binary coding which will be detected under the same conditions in the detection and decoding apparatus.

The capacity for decoding the labels according to FIG. 2 or 3 is still limited as regards an industrial and economical realization of the utilized material. It is necessary to accept a certain tolerance in the position and the extent of the cuts effected on the bands and not seek an exaggerated sensitivity of the detection apparatus. One thus would be limited in practice to five levels of amplitude per band, including here the zero level as in the embodiment described in FIGS. 2 and 3.

The labels shown in FIG. 5 are of the same type as those of FIG. 2, but here each label 1 comprises three juxtaposed metallic bands 21, 22 and 23 of the same ferro-magnetic alloy with a substantially rectangular hysteresis loop.

The labels can be introduced in a coding printer permitting independent local division of each of the elementary magnetic bands by a cut of variable extent and location. Thus, at (a) the three bands are intact which leads to maximum magnetic unbalance and maximum amplitude of the detected signal. At the opposite end, at (f), the three bands have each been divided by a large cut at their middle which substantially entirely destroys the unbalancing effect and corresponds to a zero level of signal. If one leaves each elementary band intact or cuts it at three possible places and with cuts of varying extent, one can obtain three levels of amplitude of the signal for each elementary band without counting the zero level; as the signals of each elementary band are additive in the detector since they appear in phase, it is seen that the juxtaposition of the three bands will permit defining nine levels of amplitude plus the zero level and this without having to augment the intensity of the excitation field or the sensitivity of the detection apparatus.

It is easily understood from the figures the manner of obtaining the levels of intermediate amplitude between the zero level represented at (f) and, for example, level 9 represented at (a). Thus, at (b) only the band 21 has been slightly divided and the amplitude of the signal will correspond to level 8. At (d) the band 21 has been substantially cancelled by a large cut at its middle whereas the band 22 carries a smaller cut situated near the two-thirds point of its length; the resulting signal coming from the full effect of the band 23 and a reduced effect of about one-third for the band 22 is the total signal which can be considered as representing level 4. The levels of amplitude corresponding to the other numerals represented are self-explanatory and by simple transposition, one can easily find the positions of the cuts which would lead to the level of amplitude omitted in the drawing.

Of course, the number of elementary juxtaposed bands in each composite band could also be two or four or whatever the choice depending on the particular conditions of utilization. Similarly, one could imagine that the elementary juxtaposed bands need not be of strictly identical magnetic properties as long as they have characteristics which are sufficiently close in order that the signals produced in the detecting framework by each of the elementary bands remain in phase in order to be additive in the detection apparatus.

It is also not obligatory for the levels of the amplitudes of the signals to be regularly spaced as in the described example; they could be progressively spaced to take into account a certain dispersion of the magnetic properties of the bands.

The replacement of a thin band by a composite band having, for example, three elementary bands can be applied also in the same conditions of the type of band of FIG. 3; one thus obtains the band of FIG. 6 in which each of the bands 2 carried by the label 1 is a composite band itself constituted by three metallic juxtaposed bands 24, 25 and 26 of the same ferro-magnetic alloy. The band has been introduced into a coding printer permitting local division of a type independent for the elementary magnetic bands by a cut of variable extent and placement.

Here one can easily understand from the figure, the levels of intermediate amplitude between level 9, for example, assignable to the composite band at the left and level zero represented by the third band from the left. Thus, for the composite band situated at the extreme right only the elementary band 24 has been slightly cut and the amplitude of the signal corresponds to level 8. For the second composite band from the right, the two elementary bands 24 and 25 have been divided by a large cut at their center and the resulting signal comes solely from full effect from the band 26 so that the total signal can be considered as representing level 3.

The curve shown under the label in FIG. 6 gives the appearance of the total signal as it would approximately appear, for example, on an oscilloscope.

In the simplified illustration of the detection installation in FIG. 1, the detector framework 4 carries the excitation coil 6 and the detection coil 7 normally balanced in the circuit 8. In such assembly, the field is not strictly uniform at the interior of the frame. Also the orientation of the label is uncertain according to the manner in which the sack or the package is disposed on the transporter which conveys it through the framework. As a result thereof, the same label can give very variable intensity signals. There is the danger that in certain extreme cases the signals will be difficult to detect.

Figure 7:
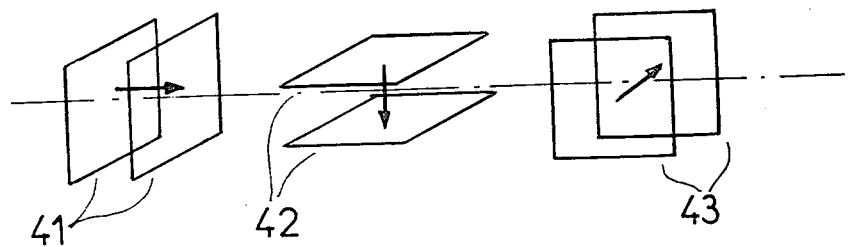
FIG. 7 diagrammatically shows an apparatus having three double frames for detection located in the path of the objects to be identified.
Figure 8:
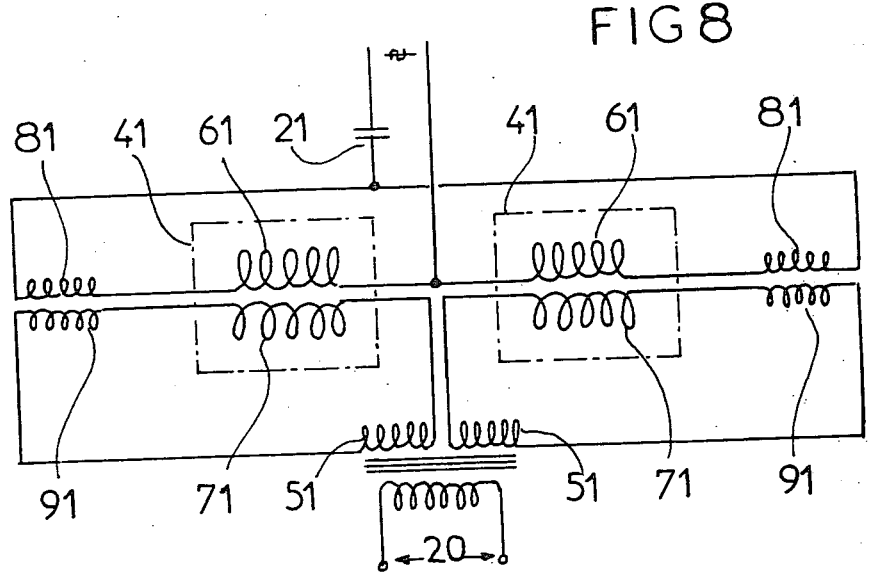
FIG. 8 is a circuit diagram for the feed and coupling of the excitation and detection of a double frame.

The apparatus described in FIGS. 7 and 8 permits obtaining signals which are substantially constant whatever the position and orientation of the parcel and its label on the transporter.

With reference first to FIG. 7, the displacement of the objects to be identified is effected along the chain dotted line. The object therefore first traverses a first group of two frames 41 each comprising, as in the framework for FIG. 1, an excitation coil and a detecting coil. The two frames 41 are disposed parallel to one another at a small spacing such that they comprise a Helmoltz coil, that is to say, the field produced by the two excitation coils is constant in direction and intensity in the space between the two coils. This field represented by the arrow in the drawing is parallel to the mean direction of displacement of the objects. The objects then pass between two similar frames 42 also mounted as a Helmoltz coil. Here the two frames are horizontal such that the magnetic field is vertical and perpendicular to the direction of displacement of the objects. Finally, there is seen a third group of two frames 43 also mounted as a Helmoltz coil, but here the frames are vertical so that the field which is produced is horizontal and perpendicular to the direction of displacement of the objects.

FIG. 8 shows in greater detail the feed and the coupling of the different coils for one group of two frames associated as Helmoltz coils. The numerals in FIG. 8 concern the particular case of the group of frames 41 but it is understood that the groups of frames 42 and 43 are connected in similar fashion.

The two excitation circuits each related to one of the frames 41 are fed in parallel from an AC source and each comprises a main excitation coil 61 contained in the frame and an auxiliary balancing coil 81, the two coils 61 and 81 being connected in series in each of the two circuits. The two detection circuits are independent and each comprises a main detection coil 71 contained in the frame 41 and an auxiliary balancing coil 91, the two coils 71 and 91 being connected in series with another output coil 51. The excitation circuit fed with AC current includes filtering circuits shown symbolically by a condenser 21.

For each of the frames 41, the balancing coil 81 of the excitation circuit and 91 of the detection circuit are inductively coupled but without an iron core. The two output coils 51 each related to one of the frames 41 are associated in parallel to form a double primary winding of a transformer and at the output 20 of the secondary of the transformer the signal is received.

It is seen that when the object and its label successively pass through or between the successive frames 41, 42 and 43, the magnetic unbalancing action of the label is successively felt with respect to the three magnetic excitation fields according to three perpendicular directions. Even if the package and its label are in poor position for the bands relative to one of the fields, it will inevitably be properly oriented with respect to one or more of the other fields. Therefore, three signals from the three groups of frames 41, 42 and 43 are received and the three signals are combined into a final signal by conventional electronic circuits. The final signal leads to an amplitude very substantially constant whatever the orientation of the label.

Of course, the invention is not strictly limited to the embodiments which have been described by way of example, but it also covers embodiments which are different only in detail by variations of realization or by the utilization of equivalent means. It is possible, for example, to produce the excitation and the detection without the object traversing the framework but by the simple passage of the object to be identified in proximity to one or a plurality of frameworks. One could then utilize fine filaments in place of thin bands.

It is not strictly indispensible for the bands or thin filaments to be carried by a label. This solution permits the code to clearly appear on the label but the filaments or bands can also be directly carried by the object to be identified if the nature thereof permits this.

Finally, the application of the process of identification is not limited to the problem of postal sorting. It could also be applied, for example, to the automatic selective opening of garage doors or for parking by affixing one coded label to the authorized vehicle and by disposing a detecting winding in the vicinity of the entrance.

One could also utilize such procedure for the marking of migratory fish and the detection of their passage in certain rivers.

What is claimed is:

1. In a process for identifying objects marked by a magnetic band or thin filament by detecting the passage of the magnetic band in a detection zone comprising at least one framework with an excitation coil fed with alternating current to produce an alternating magnetic field and a detecting coil balanced with the excitation coil such that no signal normally will appear in the absence of a magnetic body in proximity to the framework, the passage through or in proximity to the framework of an object carrying a magnetic band producing for each alternation of the excitation field an unbalance in the detecting coil and the appearance of a signal fed to an apparatus for the detection and measurement in phase with respect to the excitation field, the improvement comprising forming a reference code for an object by selectively dividing the magnetic band at a variable predetermined location by cuts of variable predetermined extent, such that at the time of passage of the band proximate the detection zone signals of variable amplitudes also predetermined are produced, and decoding the signals in the detection apparatus by measurement of said amplitudes, the object being marked with a plurality of bands or thin magnetic filaments each having different hysteresis loops characterized by different coercive fields thus permitting assignment to each object of a reference code with as many characters as bands or filaments utilized and respectively assigning each character of the reference code to a band or filament in the order of the values of their respective coercive fields, the signal corresponding to each band appearing then in the detection apparatus in the same order of dephasing as the order of the coercive fields and each with amplitudes corresponding to the values assigned at the time of coding thereby reproducing the complete code in arrangement and amplitude.

2. A process according to claim 1 wherein the code is a binary code, each band or filament being maintained intact to represent binary numeral 1 or removed or substantially divided to represent binary numeral zero.

3. A process according to claim 1 wherein each band is formed by the juxtaposition of a plurality of elementary bands of sufficiently close magnetic characteristics in order that their respective unbalancing signals are substantially in phase, each of the elementary bands being selectively divided in independent fashion.

4. A process according to claim 1 wherein the bands or magnetic filaments are disposed on a support label connected to the object and placing on the label facing each band the character to which it is assigned.

5. Apparatus for identifying objects marked by a plurality of bands or thin magnetic filaments comprising at least one framework including an excitation circuit fed with alternating current to produce an alternating magnetic field and a detecting circuit balanced with the excitation circuit such that no signal will appear in the absence of a magnetic body in proximity to the framework, the passage of an object carrying the magnetic bands in proximity to the framework producing for each alternation of the excitation field an unbalanced signal in the detecting circuit and the appearance of a signal, and means for the detection and for the measurement of the phase of said signal with respect to the excitation field, each of said magnetic bands having different hysteresis loops, each band being selectively divided at variable predetermined locations and by cuts of variable predetermined extent, said detection circuit further comprising means for measuring the amplitude of each one of the signals corresponding to each band.

6. Apparatus according to claim 5 wherein said detection circuit comprises means for binary reading of the detected signals.

7. Apparatus according to claim 5 wherein each band is a composite band constituted by the juxtaposition of a plurality of elementary bands of sufficiently close magnetic properties such that their unbalance signals are substantially in phase, each of the elementary bands being selectively and independantly divided at predetermined locations and by cuts of variable predetermined extent, said detection circuit being provided with means for measuring the total amplitude of each of the signals corresponding to each composite band.

8. Apparatus according to claim 7 wherein said framework comprises two elementary frames disposed as Helmoltz coils to produce a constant field between the two frames.

9. Apparatus according to claim 8 wherein for each elementary frame the excitation circuit comprises, in series, a main coil in the frame and an auxiliary balancing coil whereas the detection circuit comprises, in series, a main coil in the frame, an auxiliary balancing coil and an output coil for the signal, the two auxiliary coils for balancing one group of two elementary frames being inductively coupled by a coupling without iron core, the two excitation circuits of each being in each group of two elementary frames being fed in parallel whereas the two output coils constitute the two windings of the primary of a transformer whose secondary comprises a single coil at the terminals of which the output signal is received.

10. Apparatus according to claim 5 wherein the said frameworks are disposed in the path of the object in three perpendicular planes such that the three fields produced in the frames by the excitation circuits are in three perpendicular directions.

11. Apparatus according to claim 10 wherein the three output signals of the three frameworks are added to constitute the final output signal.

* * * * *